US006570061B1

(12) United States Patent
Rajewsky et al.

(10) Patent No.: US 6,570,061 B1
(45) Date of Patent: *May 27, 2003

(54) TARGETED REPLACEMENT OF AN IMMUNOGLOBULIN GENE WITHOUT ENDOGENOUS AND SELECTABLE RESIDUAL SEQUENCES IN MICE

(76) Inventors: Klaus Rajewsky, Bachemer Strasse 95, 50931, Köln (DE); Yong-Rui Zou, NAIAD, Bldg. 4, Room 111, N.I.H., 9000 Rockville Pike, Bethesda, MD (US) 20892

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/403,416

(22) Filed: Feb. 23, 1995

Related U.S. Application Data

(63) Continuation-in-part of application No. PCT/EP93/02268, filed on Aug. 24, 1993.

(30) Foreign Application Priority Data

Aug. 25, 1992 (DE) .......................................... 42 28 162

(51) Int. Cl.[7] ...................... A01K 67/00; A01K 67/027; C12P 21/00; C12N 15/00

(52) U.S. Cl. ................................ 800/18; 800/4; 800/5; 800/22; 800/24; 435/462; 435/463; 435/455; 435/320.1; 435/325; 435/326; 435/352; 435/354; 435/69.1; 435/69.2; 435/69.3; 435/69.4; 435/69.6; 435/71.1; 530/387.1

(58) Field of Search ................................ 435/69.1, 69.2, 435/69.3, 69.4, 69.6, 71.1, 172.3, 320.1, 326, 352, 354, 455, 463, 462, 325; 530/387.1; 800/2, 18, 21, 22, 25, 4, 6, 5, 24

(56) References Cited

U.S. PATENT DOCUMENTS 5,202,238 A * 4/1993 Fell et al. .................. 435/69.6
5,661,016 A * 8/1997 Lonberg et al. .......... 435/172.3

FOREIGN PATENT DOCUMENTS

| WO | WO 90/04036 | 4/1990 |
| WO | WO 90/10077 | 9/1990 |
| WO | WO 90/11354 | 10/1990 |
| WO | WO 91/01140 | 2/1991 |
| WO | WO 91/09957 | 7/1991 |
| WO | WO 91/15579 | 10/1991 |
| WO | WO 91/19796 | 12/1991 |
| WO | WO 92/20808 | 11/1992 |
| WO | WO 93/01283 | 1/1993 |

OTHER PUBLICATIONS

Berman et al. (1988) *EMBO J.* 7:727–738.
Blankenstein and Kruwinkel (1987) *Eur. J. Immunol.* 17:1351–1357.
Camerini–Otero, R. Kucherlapati (1990) The New Biologist 2(4):334–341.
Capecchi (1989) Science 244:1288.
Gu et al. (1993) *Cell* 73:1155–1164.
Koller and Smithies (1989) *P.N.A.S.* 86:8932–8935.
Mansour et al. (1988) *Nature* 336:348–352.

(List continued on next page.)

Primary Examiner—Anne Marie Wehbé
(74) Attorney, Agent, or Firm—Morrison & Foerster LLP

(57) ABSTRACT

Transgenic mice that produce high levels of humanized antibodies are described. Targeted gene replacement exchanges constant regions of the mouse immunoglobulin heavy and light chain genes with human genes, either through conventional gene targeting, or by use of the bacteriophage-derived Cre-loxP recombination system. The transgenic animals undergo antibody affinity maturation, and a class switch from the native immunoglobulin to the humanized form.

31 Claims, 8 Drawing Sheets

OTHER PUBLICATIONS

Orban et al. (1992) *P.N.A.S.* 89:6861–6865.
Rajewsky (1992) Science, 256, 483.
Sakano et al. (1981) *Nature* 290:562–565.
Sauer and Henderson (1988) *P.N.A.S.* 85:5166–5170.
Smithies et al. (1985) *Nature* 317:230–234.
Thomas and Capecchi (1987) *Cell* 51:503–512.
Thompson et al. (1989) *Cell* 56:313–321.
Yung et al. (1993) *Science* 259:984–987.
Lakso et al., (1992) "Targeted oncogene activation by site–specific recombination in transgenic mice." Proceedings of the National Academy of Sciences of USA 89(14):6232–6236.
Schulman et al., (1990) "Homologous recombination in hybridoma cells: dependence on time and fragment length." Molecular and Cellular Biology 10(9):4466–4472.

Hanks et al. (1995) "Rescue of the En–1 Mutant Phenotype by Replacement of En–1 with En–2" *Science* 269:679–682.

Marx (1995) "Knocking Genes in Instead of Out" *Science* 269:636.

Wang et al. (1996) "Functional Redundancy of the Muscle–specific Transcription Factors Myf5 and Myogenin" *Nature* 379:823–825.

O'Gorman et al., Science, vol. 251, pp. 1351–1355, Mar. 15, 1991.*

Bradley et al. 1992. Biotechnology 10: 534–539.*

* cited by examiner

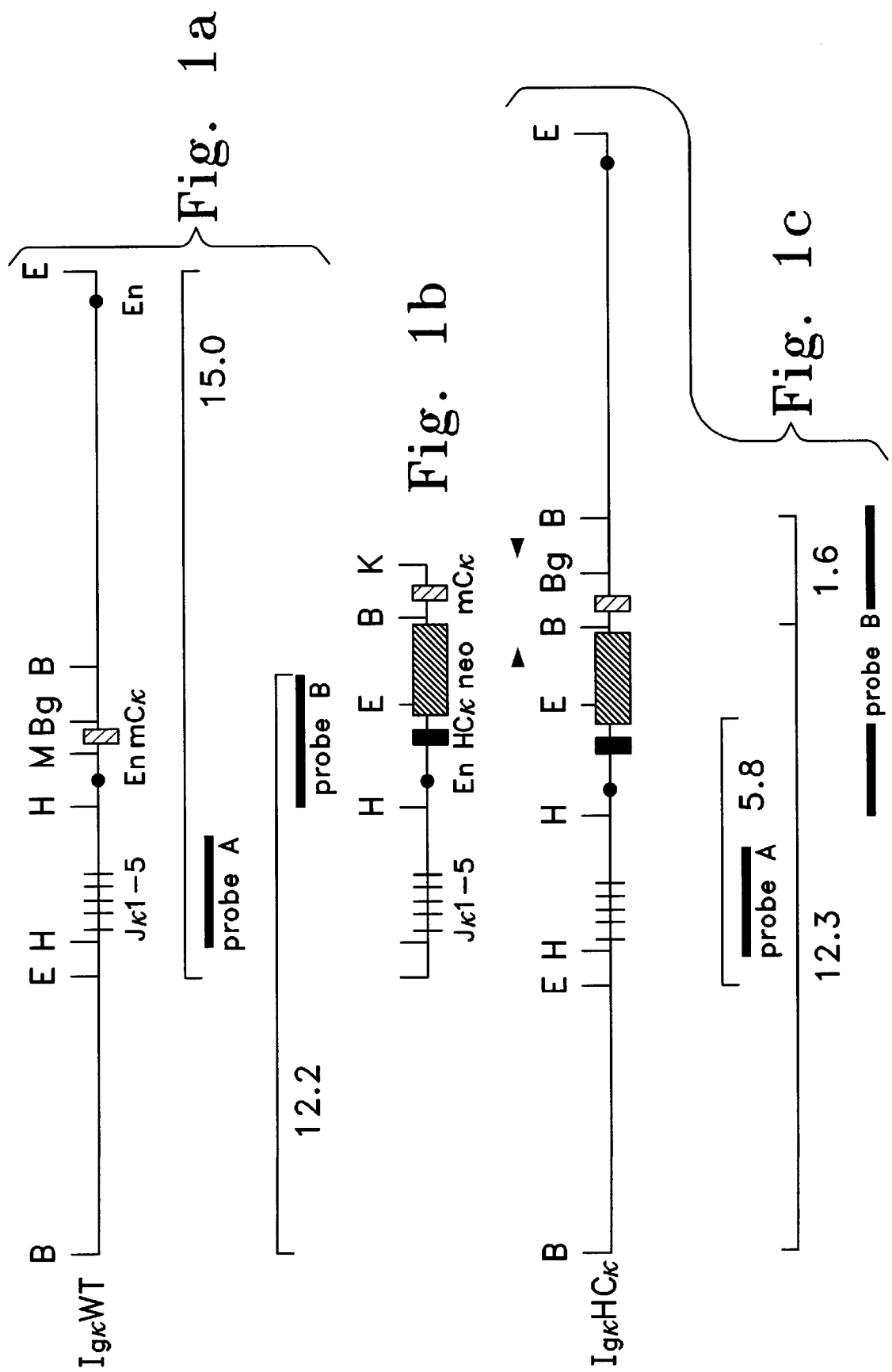

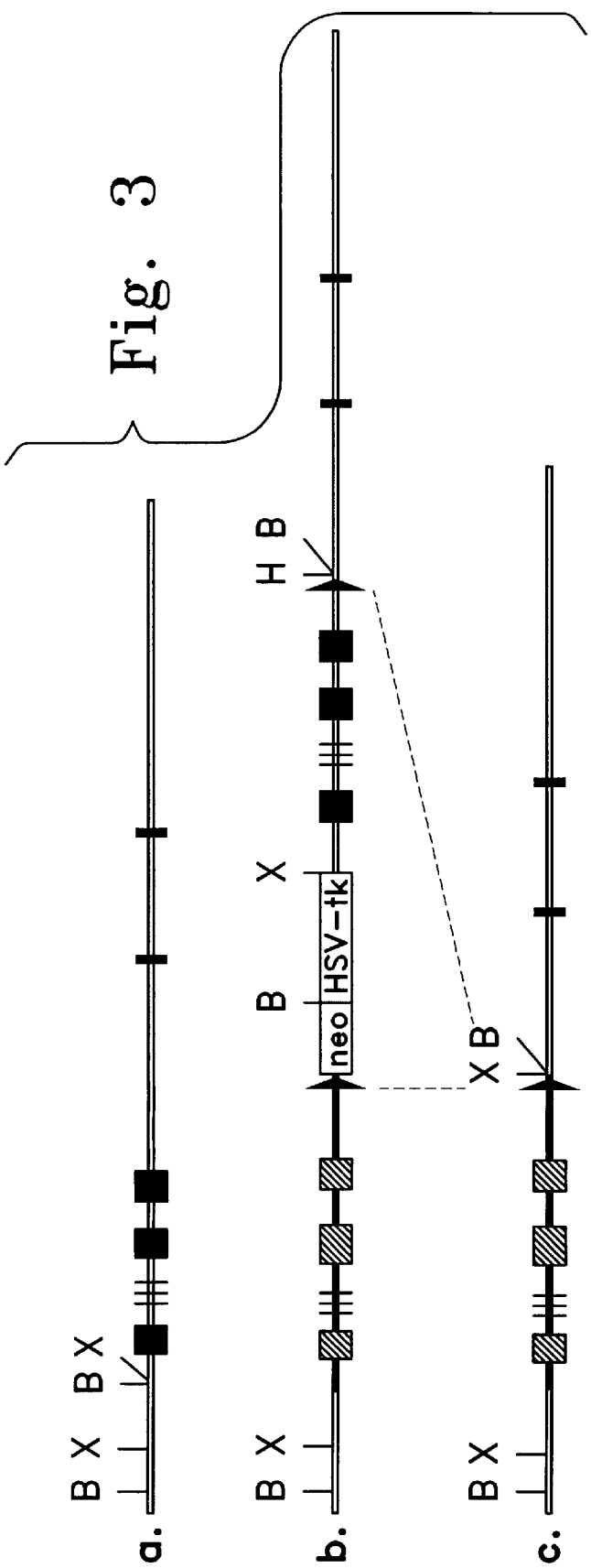

TARGETED REPLACEMENT OF AN IMMUNOGLOBULIN GENE WITHOUT ENDOGENOUS AND SELECTABLE RESIDUAL SEQUENCES IN MICE

This is a continuation-in-part of International Application PCT/93 EP 2268, with an international filing date of Aug. 24, 1993, which claims priority to German Patent Application P 42 28 162.8, filed Aug. 8, 1995.

FIELD OF THE INVENTION

The invention concerns a method for replacement of a homologous gene segment from mammals in the cell line of nonhuman mammals by homologous recombination. The invention also concerns a method for creation of a transgenic nonhuman mammal, as well as its use for expression of gene products and for testing of drugs and therapeutic models. In addition, a recombination vehicle for homologous recombination, a stably transfected cell clone and a transgenic, nonhuman mammal are disclosed.

The field of this invention is the production of humanized antibodies in a transgenic host.

BACKGROUND

Monoclonal antibodies find application in both diagnosis and treatment. Because of their capacity to bind to a specific epitope, they can be used to identify molecules carrying that epitope or may be aimed, by themselves or in conjunction with another moiety, to a specific place for diagnosis or therapy. Humanized antibodies posess significant advantages over rodent antibodies, however they have been difficult to produce in large quantities.

Various technologies have been developed to overcome problems related to the production of human monoclonal antibodies, one strategy is the generation of chimeric antibodies in which the rodent constant (C) regions of both heavy (H) and light (L) chains, with or without the framework of the variable region, are replaced by the equivalent domains or sequences of human immunoglobulin. Another strategy attempts to mimic the immune response in vitro, through bacteriophage expression of human variable region genes isolated from human B cell populations, followed by selection for rare, high affinity antibodies through antigen binding. A major drawback to these and similar approaches is the cumbersome work required to generate each specific mAb of appropriate biological function.

An ideal solution to these problems would be the generation of a mouse strain synthesizing human antibodies instead of mouse antibodies. This has been approached by introducing a mini-locus containing a few human V and C region gene segments in germline configuration into the mouse genome as a transgene. In such strains, antibodies carrying human H and L chains were indeed produced, but the levels of production were low and the repertoire of human V regions was severely limited. Thus, while the approach appears promising in principle, it is not yet at the stage to stand its final test. There is, therefore, substantial interest in finding alternative routes to the production of allogeneic antibodies for humans.

Relevant Literature

Homologous recombination between the DNA sequences present in a chromosome and new, added, cloned DNA sequences (hereafter referred to as gene targeting) permits insertion of a cloned gene into the genome of a living cell. Animals that are homozygous for the desired mutation can be obtained with this method using embryonal germ cells via chimeras (M. R. Capecchi, Science, 244, 1288 (1989)). The use of gene targeting to deactivate a gene (gene disruption) and for gene correction, i.e., incorporation of a gene segment previously not present, is described in R. D. Camerini-Otero, R. Kucherlapati, The New Biologist, 2(4), 334–341 (1990).

The insertion methods described in WO 90/11354 and WO 91/19796 in which a desired gene segment is introduced into the genome of a cell by homologous recombination are also included among the gene correction methods. In the latter method the still functional endogenous gene is removed in a second step and an endogenous gene segment thus replaced with a homologous gene segment. Moreover, WO 91/19796 discloses a virtually one-stage method, i.e., co-transfection, in which the resistance marker is not situated in the gene segment being introduced, but is introduced separately. In the examples cited in this document, however, only slightly varied homologous gene segments (maximum 2×2 base variations) are introduced, raising the question as to the extent to which a selectable recombination event can still be established during a reduction in homology (given the limited recombination frequency of the two-stage method). Nor is it demonstrated in this document whether the executed mutation of the embryonal parent cells is transferred to the cell line. Moreover, K. Rajewsky (Science, 256, 483 (1992)) suggests the use of homologous recombination for gene substitution in order, for example, to identify the function of a newly discovered gene.

In this sense, the task of the present invention was to make available a direct successful method in one step for production of genetically engineered nonhuman mammals that contain homologous gene segments from other mammals via homologous recombination.

Homologous recombination between the DNA sequences present in a chromosome and exogenous DNA sequences permits insertion of a cloned gene into the genome of a living cell. The generation of transgenic animals using this methodology is described in Thomas and Capecchi (1987) Cell 51:503–512; Capecchi (1989) Science 244:1288 and Koller and Smithies (1989) P.N.A.S. 86:8932–8935. The use of gene targeting for gene correction is described in Camerini-Otero and Kucherlapati (1990) The New Biologist 2:334–341. Targeted deletion of gene segments using the bacteriophage-derived Cre-loxP recombination system is described in Sauer and Henderson (1988) P.N.A.S. 85:5166–5170 and Orban et al. (1992) P.N.A.S. 89:6861–6865. K. Rajewsky (1992) Science 256:483 suggests the use of homologous recombination for gene substitution in order to identify the function of a newly discovered gene. Yung et al. (1993) Science 259:984–987 describe the generation of transgenic animals using the Flp/frt recombinase system.

WO 90/11354 and WO 91/19796 further describe methods of homologous recombination. In the former, a functional endogenous gene is removed in a second step after homologous recombination, thereby replacing an endogenous gene with a homologous gene segment. WO 91/19796 discloses a method in which the resistance marker is not situated in the gene segment being introduced, but is introduced separately.

The genes encoding human and mouse immunoglobulins have been extensively characterized. Berman et al. (1988) EMBO J. 7:727–738 describe the human Ig VH locus. Sakano et al. (1981) Nature 290:562–565 describe a diversity segment of the immunoglobulin heavy chain genes. Blankenstein and Kruwinkel (1987) Eur. J. Immunol. 17:1351–1357 describe the mouse variable heavy chain region.

The generation of transgenic mice bearing human immunoglobulin genes is described in International Application WO 90/10077 and WO 90/04036. WO 90/04036 describes a transgenic mouse with an integrated human immunoglobulin "mini" locus. WO 90/10077 describes a vector containing the immunoglobulin dominant control region for use in generating transgenic animals.

SUMMARY OF THE INVENTION

Animals, DNA compositions and methods are provided for the efficient production of high affinity humanized antibodies. Transgenic animals are produced through targeted gene replacement. The native immunoglobulin constant region is replaced with the corresponding human gene segment. Of particular interest is the use of non-mammalian recombinase systems in embryonic stem (ES) cells, which allows for a convenient replacement process. Humanized antibodies are made at a high level and efficiency. In a preferred embodiment, transgenic animals are obtained that undergo antibody affinity maturation and a class switch from the native immunoglobulin to the humanized form. A method was found by the applicant that permits targeted replacement of individual gene segments in the cell line of a mammal in one step with gene segments of other species.

The present invention thus concerns a method for replacement of a gene or gene segment in the cell line of a nonhuman mammal with a homologous gene or a homologous gene segment of another mammal, in which (i) an embryonal parent cell line is transfected with a selectably marked recombination vehicle; (ii) stably transfected cell clones are selected for the presence of the marker gene; (iii) they are subjected to targeted selection by PCR and/or Southern Blot; (iv) these are injected into the blastocysts of the nonhuman mammal; (v) the blastocysts are transferred to surrogate mothers, characterized by the fact that the endogenous gene or the endogenous gene segment is functionally replaced in one step by the homologous gene or the homologous gene segment in the recombination event by means of the selectably marked recombination vehicle.

It is preferred according to the present invention that the introduced gene or the introduced gene segment originate from humans and that the nonhuman mammal be a rodent, especially a mouse.

Genes or gene segments that code for proteins involved in the immune system, the nervous system, especially signal-mediating and adhesion molecules, virus receptors, the blood-forming system and support tissue, especially muscles, tendons and bones may also be replaced according to the subject methods. Those genes and gene segments that code for protein of the immune system are particularly preferred, especially antibody genes, T-cell receptor genes, cytokines, cytokine receptor genes, MHC genes, adhesion molecule genes and genes of signal-mediating molecules.

An antibody gene segment of the mouse is replaced by an antibody gene segment of man in a special variant of the present invention.

The selectably marked recombination vehicle according to the invention is a replacement vector and carries the gene or gene segment to be introduced, sequences that are homologous to the sequences that flank the endogenous DNA segment to be replaced and a marker gene, especially neomycin or hygromycin, neomycin being preferred. Moreover, the recombination vehicle can also contain viral recognition sequences (for example SV40), additional sequences to amplify gene expression, target sequences for pro- and eukaryotic recombination systems. The latter sequences, especially the Cre recognition sequence LoxP or the flip recognition sequence-Frt, can be used for targeted removal of marker genes, as well as any still remaining non-functional target gene segments. In this fashion it is possible to replace in the first step the endogenous gene segment with a homologous gene segment of another mammal and to remove the remaining residues in a second step by means of a selectively functioning recombinase (H. Gu et al., Cell, 73, 1155–1164 (1993)). The remaining residue is selectively removed in this method and only the desired recombination can occur, in contrast to the "hit and run" method described in WO 91/19796.

The selectably marked recombination vehicle in a preferred variant of the present invention is the plasmid pTZ$_2$-CkN (PA$^-$)(DSM 7211).

Another object of the present invention is a recombination vehicle for homologous recombination that contains the gene to be replaced or the gene segment to be replaced and a selectable marker gene. The recombination vehicle can also contain the recognition, amplification and/or target sequences already mentioned.

Another object of the present invention is the stably transfected cell clone produced by the method according to the invention, as well as a method for creation of a transfected, nonhuman mammal. According to the latter method the stably transfected cell clones according to the invention are injected into mouse blastocysts, these blastocysts are transferred to the surrogate mother, the born chimeral animals are mated and their offspring selected for the presence of the mutation.

Transgenic nonhuman mammals that can be obtained in this fashion are also an object of the present invention.

Another object of the present invention is the use of the selectively mutated, transgenic nonhuman mammal for expression of gene products of another mammal instead of the product coded by the original gene segment and for testing of drugs and therapeutic models. The use of these gene products to produce humanized monoclonal antibodies and for virus production is particularly preferred in the sense of the present invention.

The method according to the invention permits replacement of genes or gene segments in the cell line of nonhuman mammals with a homologous gene or a homologous gene segment of another mammal in one step. Animals that are homozygous for the desired mutation are obtained via chimeras and can be used for expression of gene products of another animal instead of the endogenous gene or for testing of drugs and therapeutic models.

BRIEF DESCRIPTION OF THE DRAWINGS

FIGS. 1A to 1C are schematics of the human and mouse immunoglobulin kappa region loci. FIG. 1A shows the germline mouse $C_\kappa$ locus. FIG. 1B shows the subject targeting vector. FIG. 1C shows the mouse locus after the recombination event in which $mC_\kappa$ is replaced by $HC_\kappa$. The cleavage sites for restriction enzymes (B, BamHI; E, Eco RI; H, Hpa I; M, Mst II; Bg, Bgl II; K, Kpn I) are indicated. The DNA probes used for the Southern blot analyses are shown, as well as the fragments obtained. FIG. 1C shows the primers, designated by arrows, used for amplification.

FIG. 2 is a point diagram FIGS. 2a and 2c) and a homozygous mouse mutant ($HC_\kappa/HC_\kappa$; FIGS. 2b and 2d) were stained with antibodies specific for the B-cell antigen CD45R (B220), and antibodies specific for either mouse (FIG. 2a and 2b) or human (FIGS. 2c and 2d) kappa chains. The cells were analyzed in a flow cytometer.

FIGS. 3A to 3C are schematics of the human and mouse IgG1 locus during homologous recombination using a Cre recombinase. FIG. 3A shows the germline mouse IgG1 locus, with the exons marked with boxes. The symbols B and X signify BamHI and XbaI restriction sites. FIG. 3B shows the locus after replacement with the human gene fragment. The black triangles designate LoxP recognition sequences. FIG. 3C shows the locus after removal of the region flanked by LoxP by recombinase Cre.

DESCRIPTION OF THE SPECIFIC EMBODIMENTS

Figure 2B:
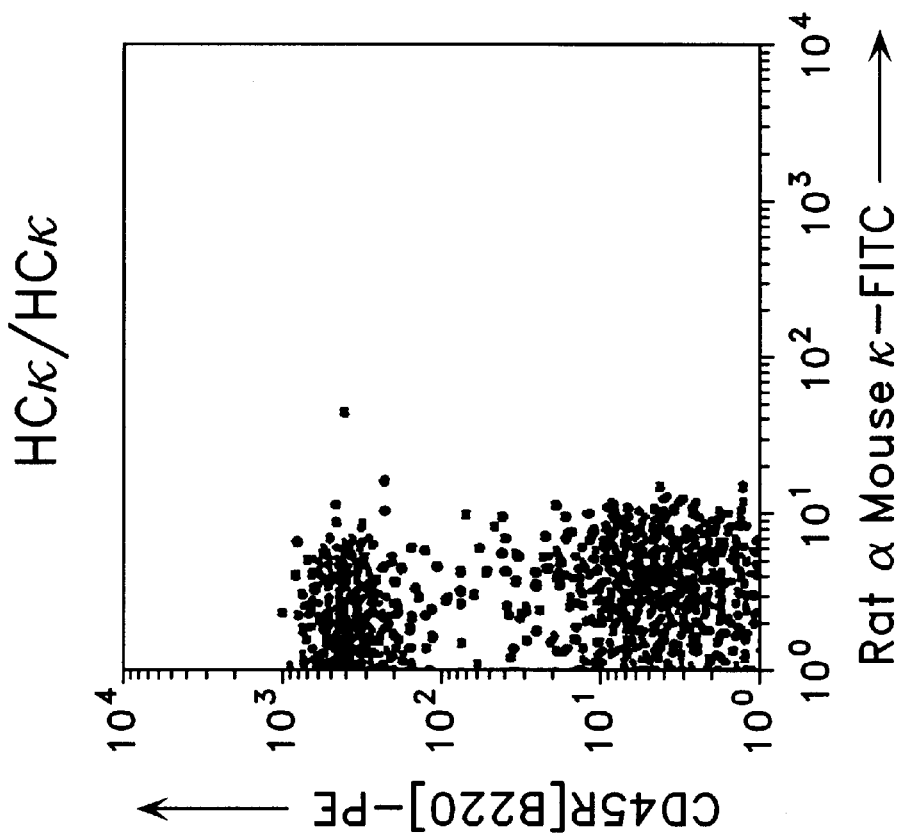
FIGS. 2a–2d show point diagrams of antibody staining for the presence of human kappa chain in the transgenic mice. Spleen cells of a wild type mouse (WT/WT.
Figure 2A:
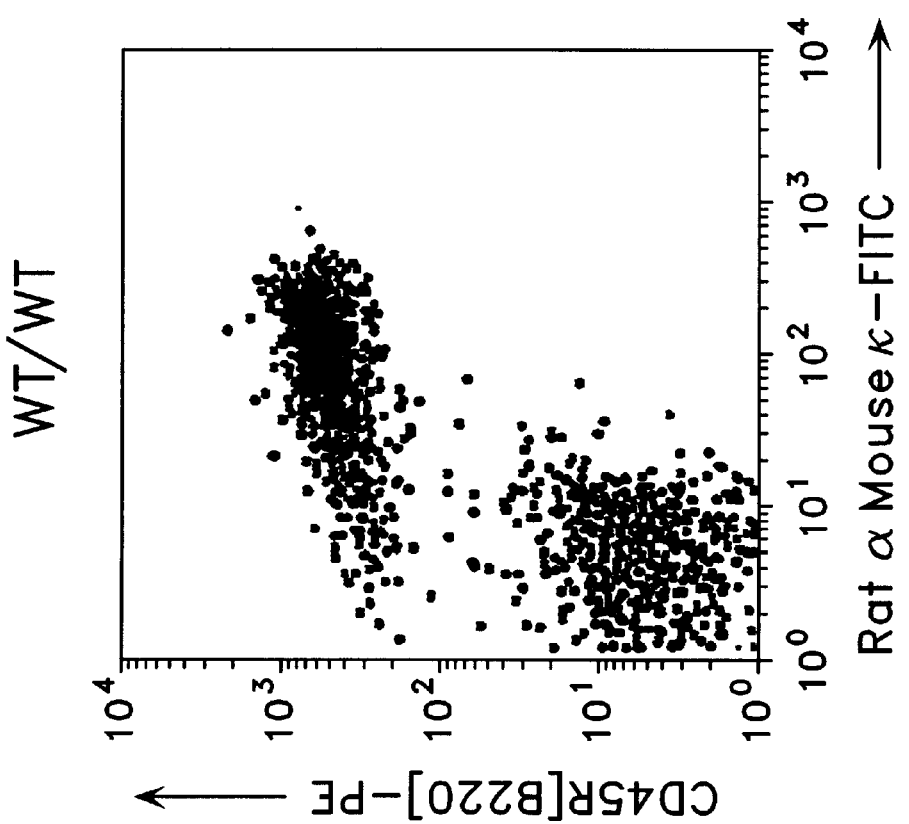
Figure 2D:
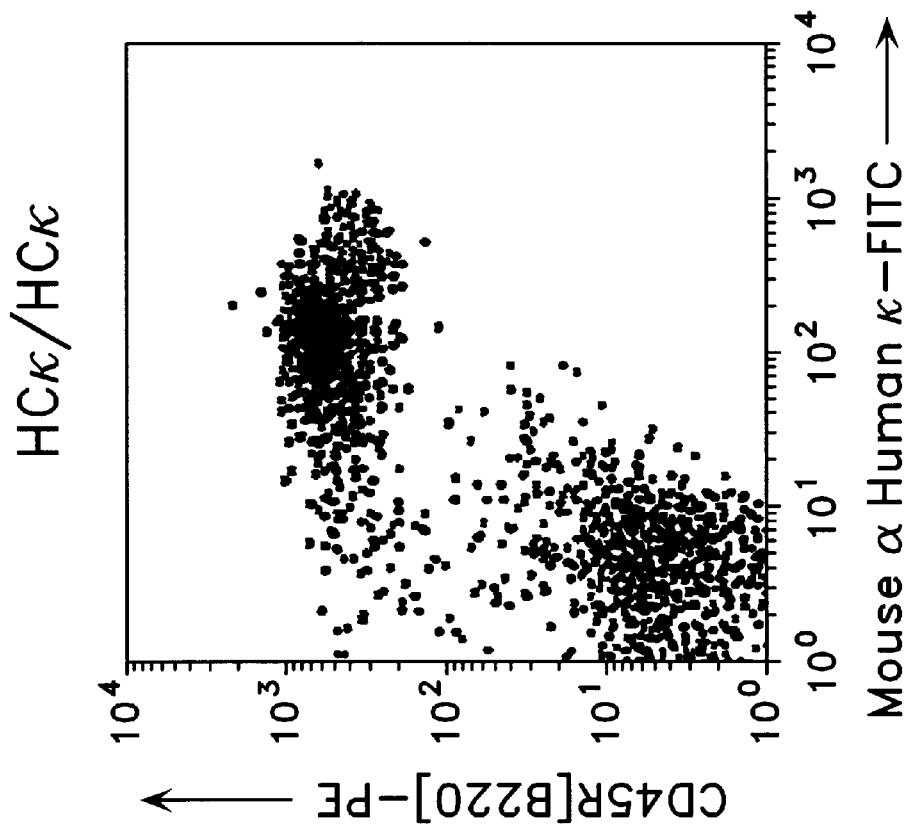
Figure 2C:
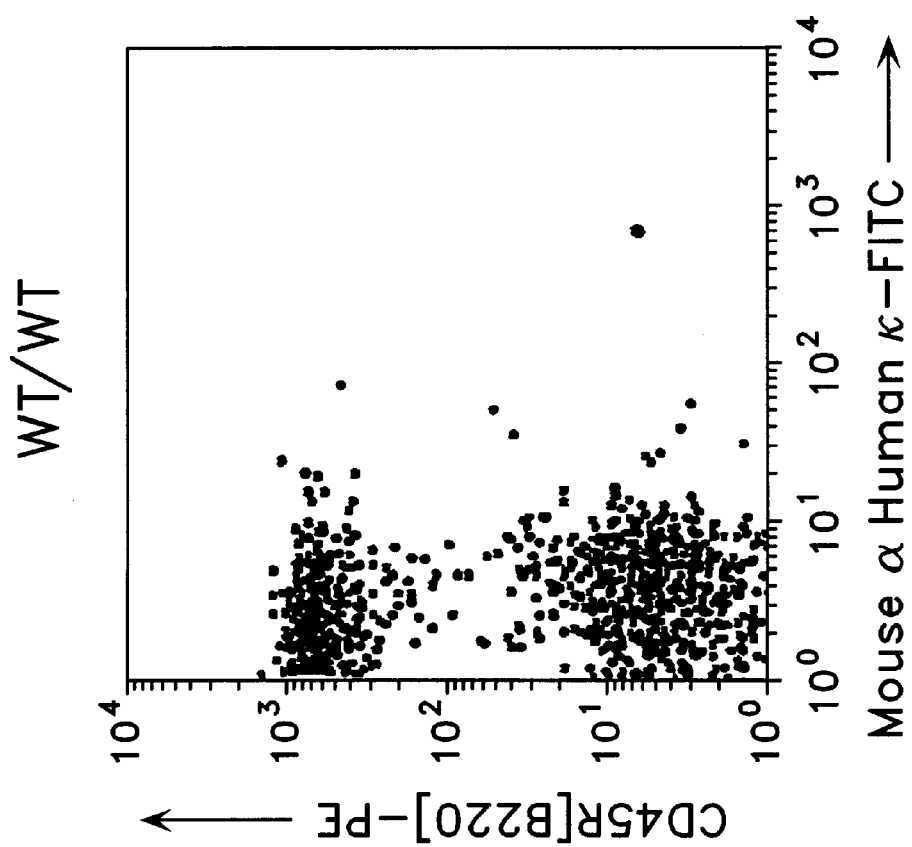

Animals, DNA compositions and methods are provided for the efficient production of high affinity humanized antibodies in a transgenic animal. Targeted gene replacement is used to exchange the native immunoglobulin constant region with the corresponding human gene segment. The replacement may be effected with conventional gene targeting or with the a non-mammalian recombination system, such as bacteriophage-derived Cre-loxP or flp/frt. Transgenic animals are obtained that produce high affinity antibodies with human constant region sequences. During in vivo affinity maturation, animals with a native $C\mu$ region are able to class switch to a transgenic C region, e.g. $C\gamma$, $C\alpha$, $C\delta$ or $C\epsilon$.

The subject invention provides for the production of polygonal humanized anti-serum or humanized monoclonal antibodies. The humanized antibodies have a human constant region and a host variable region. The humanized antibodies are produced at a level comparable to native antibodies. Humanized light chains will usually be present in serum at concentrations of at least about 500 µg/ml, more usually at least about 1 mg/ml. The serum concentration of humanized heavy chains is dependent on class switching and will usually be present at concentrations of at least about 50 µg/ml, more usually at least about 100 µg/ml. The genes encoding the humanized antibodies are able to undergo somatic hypermutation, thereby allowing for B cell selection and affinity maturation.

The subject transgenic animals have a native immunoglobulin (Ig) constant region gene functionally replaced with a human constant region gene, that is, the human constant region segment replaces the native gene segment in the genetic recombination and expression events associated with an antibody response. The native gene may be deleted or inactivated. The constant region gene is herein defined as the constant region exons, and optionally including introns, encoding, the secreted portion of a mature immunoglobulin chain. In a preferred embodiment, the host transmembrane and cytoplasmic portion will be retained. An intact switch region, either human or from the native gene, will be present at the heavy chain locus.

For most applications, it is desirable to have the genes for both the Ig heavy and light chain constant regions replaced with human genes. Either of the human light chain constant region genes, i.e. $C\kappa$ and $C\lambda$, may be used to replace a host light chain constant region. At the host heavy chain locus, at least one of the isotypes will be functionally replaced, e.g. $C\mu$, $C\delta$, $C\gamma$, $C\alpha$ or $C\epsilon$. The transgenic human gene may be the counterpart to the native gene, e.g. $C\gamma1 \rightarrow C\gamma1$, or may be a different isotype. Preferably, the replaced host region will be other than $C\mu$. Of particular interest are the $\alpha$ and $\gamma$ constant regions, which may be interchanged, e.g. $C\gamma1 \rightarrow C\alpha$; $C\gamma2 \rightarrow C\alpha$; $C\gamma3 \rightarrow C\alpha$; $C\gamma4 \rightarrow C\alpha$; $C\alpha \rightarrow C\gamma1$, etc., $C\gamma1 \rightarrow C\epsilon$, etc.; $C\alpha \rightarrow C\epsilon$, and the like.

A number of strategies may be employed to achieve the desired transgenic hosts. Various hosts may be employed, particularly murine, lagomorpha, ovine, porcine, equine, canine, feline, or similar animals. For the most part, mice have been used for the production of B-lymphocytes that are immortalized for the production of antibodies. Since mice are easy to handle, can be produced in large quantities, and are known to have an extensive immune repertoire, mice will usually be the animals of choice. Therefore, in the following embodiments, the discussion will refer to mice, but it should be understood that other animals, particularly mammals, may be readily substituted for the mice, following the same procedures.

Methods for producing transgenic animals are known in the art. A host embryonic cell, generally an embryonic stem cell line, is transfected with the recombination vector. Where the exogenous gene is Ig heavy chain, the host coding region for the exons CH1, CH2, hinge, CH3 and CH4 will be inactivated by a lesion that results in the loss of transcription. Preferably, the heavy chain cytoplasmic and transmembrane domains of the constant region will continue to be expressed. Where the exogenous gene is an Ig light chain, at least one of the host Ig light chain constant regions, e.g. IgC$\kappa$ or IgC$\lambda$, will be similarly inactivated. Such a lesion may take the form of a deletion in the target gene, an insertion of a foreign gene, or a replacement, where a deletion is made in the endogenous gene and is replaced with exogenous sequences. In a preferred embodiment, the vector will include loxP sites, allowing for the deletion of the host coding region through the action of Cre recombinase.

The vector will usually include a selectable marker, the human constant region gene, and regions of homology to the host target locus, i.e. the region of the chromosome that will be replaced with the human sequence. The homologous region will usually be at least about 100 bp, more usually at least about 1 kb, and usually not more than about 10 kb in length. If a non-mammalian recombinase, e.g. Cre, Flip, etc., is to be used, the homologous region will contain the entire region to be replaced, having recombinase recognition sites, e.g. loxP,frt, flanking the selectable marker and homologous region.

Various markers may be employed for selection. These markers include the HPRT minigene (Reid et al. (1990) *Proc. Natl. Acad. Sci. USA* 87:4299–4303), the neo gene for resistance to G418, the HSV thymidine kinase (tk) gene for sensitivity to gancyclovir, the hygromycin resistance gene, etc. The recombination vehicle may also contain viral recognition sequences, e.g. SV40, etc., additional sequences to amplify gene expression and the like.

After transfection, the embryonic stem cells are grown in culture under conditions that select for cells expressing the selectable marker gene. Those cells are then screened to determine whether the recombination event took place at the homologous chromosome region. Such screening may be performed by any convenient method, including Southern blotting for detection of differentially sized fragments, PCR amplification, hybridization, etc.

The cells may be further manipulated to homogenotize the recombination (see, for example PCT/US93/00926) or to induce deletion of the host target sequence. Where the vector includes recognition sites for an exogenous recombinase, deletion between the recognition sites Occurs by exposure of the DNA to the recombinase, which is conveniently achieved by transfecting the cell with an expression vector encoding the recombinase, and then inducing transient expression. The cells may then undergo another round of selection for those having the deletion.

Cells having the desired recombination are injected into blastocysts of the host mammal. Blastocysts may be obtained from females by flushing the uterus 3–5 days after ovulation. At least one, and up to thirty, modified embryonic stem cells may be injected into the blastocoel of the blastocyst. After injection, at least one and not more then about fifteen of the blastocysts are returned to each uterine horn of pseudo-pregnant females. Females are then allowed to go to term, and the resulting litter is screened for mutant cells having the construct.

Subsequent breeding allows for germ line transmission of the altered locus. One can choose to breed heterozygous offspring and select for homozygous offspring, (i.e. those having the human gene segment present on both chromosomes) from the heterozygous parents, or the embryonic stem cell may be used for additional homologous recombination and inactivation of the comparable locus. The animal thus generated may serve as a source of embryonic cells for further replacement of Ig loci.

The subject invention provides for the production of polyclonal humanized anti-serum or humanized monoclonal antibodies or antibody analogs. Where the mammalian host has been immunized with an immunogen, the resulting humanized antibodies may be isolated from other proteins by means of an an Fc binding moiety, such as protein A or the like. Of particular interest is the production of antibodies to proteins or other molecules of human origin that are not normally capable of raising an antibody response in humans. Proteins found in blood or the surface of human cells are useful as immunogens. Tumor antigens of human origin may also be a source of antigens. Also of interest is the production of antibodies to various pathogens that infect humans, e.g. viruses, fungi, protozoans, bacteria, etc. The transgenic animal is able to respond to immunization with specific antigens by producing mouse B-cells expressing specific humanized antibodies. The B-cells can be fused with mouse myeloma cells or be immortalized in any other manner for the continuous stable production of humanized monoclonal antibodies.

The following examples are offered by way of illustration and not by way of limitation.

EXPERIMENTAL

Gene Replacement with the Human $C_K$ Gene Segment

The plasmid pTZ-$HC_K$ was constructed, in which a 727 base pair long SphI-HhaI fragment containing the $C_K$-exon from the vector pC-2 (H.-G. Klobeck et al. (1984) *Nucleic Acids Research* 12:6995–7006) was inserted between the SphI and PstI cleavage sites of the polylinker of plasmid pTz-19(R) (Pharmacia LKB, Catalog No. 27-5986-01, Pharmacia LKB GmbH, P.O. Box 5480, Munzinger Str. 9, 7800 Freiburg).

The plasmid pTZ-$HC_K$-$mC_K$-$mC_K$5' was constructed, in which a 1.2 kb HindIII-MstII fragment of vector p$HBC_K$ (S. Lewis et al. (1982) *Cell* 30:807–816) that contains the intron enhancer element was inserted between the HindIII and SphI cleavage sites of plasmid PTZ-$HC_K$.

The plasmid pTZ-5'$HC_K$Neo was constructed in which a 1.1 kb XHOI-BamHI fragment that contains the neomycin-resistance gene from plasmid pMCINeo (Stratagene, Catalog No. 213201, Stratagene GmbH, P.O. Box 105466, Im Weiher 12, 6900 Heidelberg) was inserted between the SalI and BamHI cleavage sites of vector pTZ-$HC_K$-$mC_K$5'.

The plasmid pTZ-5'$HC_K$Neo was constructed in which a 2.8 kb long HindIII fragment of plasmid $PHJ_K$ (S. Lewis et al., loc. cit.) that contains the J 1–5 elements was inserted in the HindIII cleavage site of plasmid pTZ-5'$HC_K$Neo.

The plasmid pTZ$_2$-CkN (PA–) (DSM 7211), which was used for gene substitution, additionally contains a 427 bp long fragment between the Bam HI and KpnI cleavage sites of plasmid pTZ-5'-$HRC_K$Neo, which was amplified by means of the polymerase chain reaction from mouse cell line DNA. The following primers were used to amplify this fragment from the mouse cell line DNA:

5'-CAGGATCCAACTGTATCCATC (SEQ ID NO:1) hybridizes 12 base pairs after the beginning of the $C_K$-exon; 5'-GAGGTACCAAGGAAAGGGAGG (SEQ ID NO:2) hybridizes 137 base pairs after the stop codon TAG of the $C_K$-exon.

Homologous Recombination

The method of homologous recombination by means of replacement vectors has been previously described (Kitamura et al.(1991) *Nature;* Kuhn et al. (1991) *Science;* Kitamura et al. (1992) *Cell*). The vector used for homologous recombination contains a 4.5 kb segment of genomic DNA of the murine kappa gene ($MC_K$), containing the gene segment $J_K$ 1–5, the kappa-intron-enhancer and the 3' untranslated region present from the $mC_K$ gene without the polyadenylation site. The human kappa gene ($HC_K$) and a neomycin gene lacking its own polyadenylation site were inserted between the MstII and HpaI restriction cleavage sites, and the splice donor site of $mC_K$ present between MstII and HpaI was removed (FIG. 1). Since the neomycin gene carries no polyadenylation site on the vector, a homologous recombination event was selected for because a neomycin-resistant cell clone can only form if the vector integrates before a polyadenylation site in the genome. This occurs if the vector integrates at the homologous site.

The vector was linearized and incorporated by electroporation into the embryonic stem cells (ES) of the mouse. Neomycin-resistant ES cells carrying the homologous recombination event were identified by polymerase chain reaction and subsequent Southern blot. $2\times10^7$ ES cells were transfected in one experiment. Out of 480 neomycin-resistant ES cells, one carried the planned mutation, as shown in FIG. 1.

In order to investigate expression of the humanized antibody, chimeric mice were produced by means of an ES cell clone. These chimeric mice were mated with C57BL/6 mice. Mice carrying the mutation were mated in the next generation. Mice born in the following generation carried the two unaltered mouse kappa loci (WT) (25%), carried two mutated loci ($HC_\kappa$) (25%), or carried one unaltered and one mutated locus (50%).

A wild type mouse (WT/WT) and a mouse homozygous for the mutation ($HC_\kappa/HC_\kappa$), were compared in their ability to produce antibodies. To demonstrate that the $HC_\kappa$ gene is used for antibody formation in the homozygous mouse mutants, the concentration of antibodies that carry the constant region of the human kappa gene were determined in the serum of the mice. Humanized antibodies are not detectable in a wild type mouse, where the limits of detection are about 250 ng/ml human $C_\kappa$ protein. A concentration of 178 µg/mL was found in the sera of mice carrying one $HC_\kappa$ allele, while a concentration of 2860 µg/ml was found in the homozygous mice. For comparison, normal human serum contains about 15,000 µg/ml $C_\kappa$.

The direct proof that the $HC_\kappa$ gene functionally replaced the $mC_\kappa$ gene is shown by an analysis of antibody-producing cells (B-lymphocytes) in the mouse. Resting B-lymphocytes carry antibodies on their surface that they express after gene rearrangement. These antibodies can be detected by labeled antibodies specific for light chains. FIG. 2 depicts the results of an experiment in which antibodies specific either for the kappa chain of the mouse or for the kappa chain of humans. The cells were stained with a phycoerythrin (PE) conjugated antibody that recognizes all B-cells (anti CD45R(B220)). At the same time, the cells were stained with a fluorescein conjugated antibody specific for the constant region of the kappa-light chain. The data shows that B-lymphocytes in the transgenic mouse express antibodies with the human kappa chain and that the kappa chain of the mouse is no longer used.

Gene Replacement with the Human Cγ gene

To construct the vector pG1, the plasmid pG1A that codes for the homologous region of the short arm of IgG1 (which contains the mouse $_{\gamma1}$-gene and its flanking regions) was first isolated by PCR. For this purpose, a mixture of 10 pmol of the following primers: TTATCGATACAGAGGCTCAAC-CTACAAA (SEQ ID NO:3) and CCAAGCTTCGC-TACTTTTGCACCCTT (SEQ ID NO:4), as well as 10 ng of the plasmid DNA, were subjected to 25 cycles at 94° C. (1 min), 69° C. (1.5 min) and 74° C. (2 min). To produce the p5'HROGNT vector, the isolated homologous region was cloned in a $neo^r$-tk cassette (H. Gu et al. (1993) Cell 73:1155–1164) that had an Frt site (O'Gorman et al. (1991) Science 251:1351) on the 5' terminus. The p5'HROGNT vector was partially digested with BamHI and then with XhoI. A 1.2 kb BamH-XhoI fragment that contains a $neo^r$ gene having a loxP site on its 5' terminus was isolated from the plasmid pGH1 and cloned to produce the vector pG1 in the digested p5'HROGNT vector.

To produce vector PG2, the human $_{\gamma1}$ gene that codes for the secretory form of human IgG1 was subcloned in the pG1 vector. For this purpose, a 2.1 kb HindIII-PvuII fragment that contains the human $_{\gamma1}$ gene was isolated from the plasmid pTJ1B (A. Kudo et al. (1985) Gene 33:181). Another fragment that contains the $neo^r$ gene and part of the tk gene was isolated from the pG1 plasmid by XhoI digestation, subsequent $T_4$ polymerase replenishment and digestion with BglII. The pG1 vector was also partially digested with HindIII and then with XhoI-BglII. These three fragments were ligated to construct the pG2 vector.

To construct vector pG3, a loxP site was subcloned before the mouse $_{\gamma1}$ membrane exons. For this purpose, the plasmid pTZ-3'$_{\gamma1}$ (4.3) and the plasmid pGEM30 (H. Gu et al., Cell, 73, 1155–1164 (1993)) were partially digested with EcoRI and SalI and were ligated together. The plasmid pTZ-3'$_{\gamma1}$ (4.3), which contains two membrane exons of the mouse $_{\gamma1}$ gene, was produced from a 1.5 kb SacI-EcoRI fragment of plasmid pGA1 and a 2.8 kb EcoRI fragment of the bacteriophage $ch_{\gamma1-3}$ (A. Schimizu et al., Cell, 28, 499 (1982)).

To construct the entire 3' homologous region of the gene substitution vector, the vector pGH2 (which contains a genomic 6.3-XbaI-EcoRI genomic DNA fragment) including the mouse $_{\gamma1}$ gene in the secretory and membrane form, was digested with SacI, replenished with $T_4$ polymerase and then digested with BglII. The pG3 vector was cleaved with XhoI, replenished with $T_4$ polymerase and then cleaved with BglII and SphI. To construct vector pG4, the two fragments so obtained were ligated.

To construct the gene substitution vector pG5, the vector pG4 was cleaved with ClaI and XhoI, the vector pG2 was cleaved with ClaI and SalI, and the cleaved vectors were ligated together.

Homologous Recombination

For homologous recombination, the vector pG5 was linearized by ClaI digestion and introduced to embryonic parent cells of the mouse by electroporation as described above.

In an additional step, the Cre recombinase was transiently expressed in the embryonic parent cells (H. Gu et al. (1993) Cell 73:1155–1164). The recombinase then removes the region flanked by the loxP recognition sequences with higher efficiency (FIG. 3). A mouse mutant that is homozygous for the mutation was then created in accordance with the method described above for the $C_\kappa$ locus chimeric mice.

The demonstration that the mouse gene that normally codes for the constant region of the IgG1 gene was replaced by the corresponding region of the human gene was confirmed by detection of human IgG1 in cultures of B-cells of the corresponding chimeric mouse: concentrations of 2 µg/ml of human IgG1 were measured in cultures from three mice, whereas the values were below the detection limit of 0.1 µg/ml in the control cultures.

These examples show that it is possible by homologous recombination to replace antibody genes or gene segments from one species with those of another species in a single step. In addition, by mating a mouse having the $C_\kappa$ replacement with a mouse having the Cγ replacement, a mouse mutant is obtained in which both the $C_\kappa$ gene and the $C_{\gamma1}$ gene are of human origin. Such a mouse mutant is therefore suitable for the production of humanized monoclonal antibodies.

The plasmid (pTZ2-CkN (PA-)) used for gene substitution was filed with the German Collection of Microorganisms and Cell Cultures GmbH, Maschorder Weg 1b, W-3300 Braunschweig as *E. coli* strain DSM 7211 on Aug. 18, 1992.

Analysis of Human Cκ Antibody Production

In the transgenic mouse strain, substantial numbers of B-cells which express humanized κ chains on the cell surface are generated. In the blood of 8-week-old transgenics, the levels of antibodies bearing humanized light chains were approximately 2 mg/ml, compared to 3.5 mg/ml κ chain bearing antibodies in control mice of the same age.

The data in Table 1 is a representation of different lymphocyte populations in the spleen of normal and control mice. Single cell suspensions were prepared from the spleens of individual mice at the age of 8 weeks. Cell numbers were determined by hemocytometer. Cells were stained with FITC-conjugated anti-mouse λ, anti-mouse κ, anti-human κ, or anti-CD3, respectively. The cells were also stained with a PE-conjugated anti-CD45/B220 antibody. The flow cytometric analysis was performed on a FACScan.

TABLE 1

|  | +/+ (wild type) | CκR/+ | CκR/CκR |
|---|---|---|---|
| No. of nucleated cells (× $10^7$) | 25.2 ± 2.5 | N.D. | 17.3 ± 1.9 |
| No. of T cells (× $10^7$) | 7.5 ± 0.9 | N.D. | 7.7 ± 0.5 |
| No. of B cells (× $10^7$) | 17.7 ± 1.5 | N.D. | 9.5 ± 2.4 |
| λ/B cells (%) | 4.9 ± 0.4 | 5.6 ± 0.5 | 17.2 ± 2.8 |
| Mouse κ/B cells (%) | N.D. | 85.4 ± 1.5 | <1 |
| Human κ/B cells (%) | <1. | 6.1 ± 1.9 | 89.1 ± 8.1 |

N.D. not determined.

The distribution of antibody isotypes was similar in mutant and wild-type animals. Although in the transgenics about 10% of the antibodies carry $\gamma_1$ chains, a large fraction of the IgG antibodies are associated with humanized κ chains, because IgG represents the major isotype in the serum. The presence of serum IgG antibodies which carry the humanized light chains indicates that B cells expressing the latter can be triggered by environmental antigens to contribute to antibody responses.

Analysis of Antigen Specific Response

To investigate whether the CκR strain would have its natural antibody repertoire at its disposal, and whether it would be capable of generating antigen-specific antibodies upon immunization with different antigens, the human Cκ mice were immunized with phosphorylcholine (PC) coupled to keyhole limpet hemocyanin (KLH), 2-phenyl-5-oxazolone (phOX)-chicken serum albumin (CSA) and chicken γ-globulin (CG). Eight-week old mice received intra-peritoneal injections of 100 µg alum precipitated antigen, mixed with $10^9$ Bordatella pertussis cells.

The concentration of specific antibodies was determined by ELISA. Plastic plates were coated with CG, KLH, OX-BSA or PC-BSA (10 µg/ml). Diluted serum samples were added, and bound antibodies were detected by means of biotinylated antibodies for the determination of mouse κ, human κ, IgM, and for total IgG. The relative concentration of OX-specific IgG or PC-specific IgM was determined by comparison to standard monoclonal OX- or PC-specific antibodies of the same isotypes. The relative concentration of CG- or OX-specific κ bearing antibodies as well as KLH-binding IgM or IgG are shown as arbitrary units defined by taking the value of the serum from a pre-immune normal or mutant animal as one unit.

Figure 4:
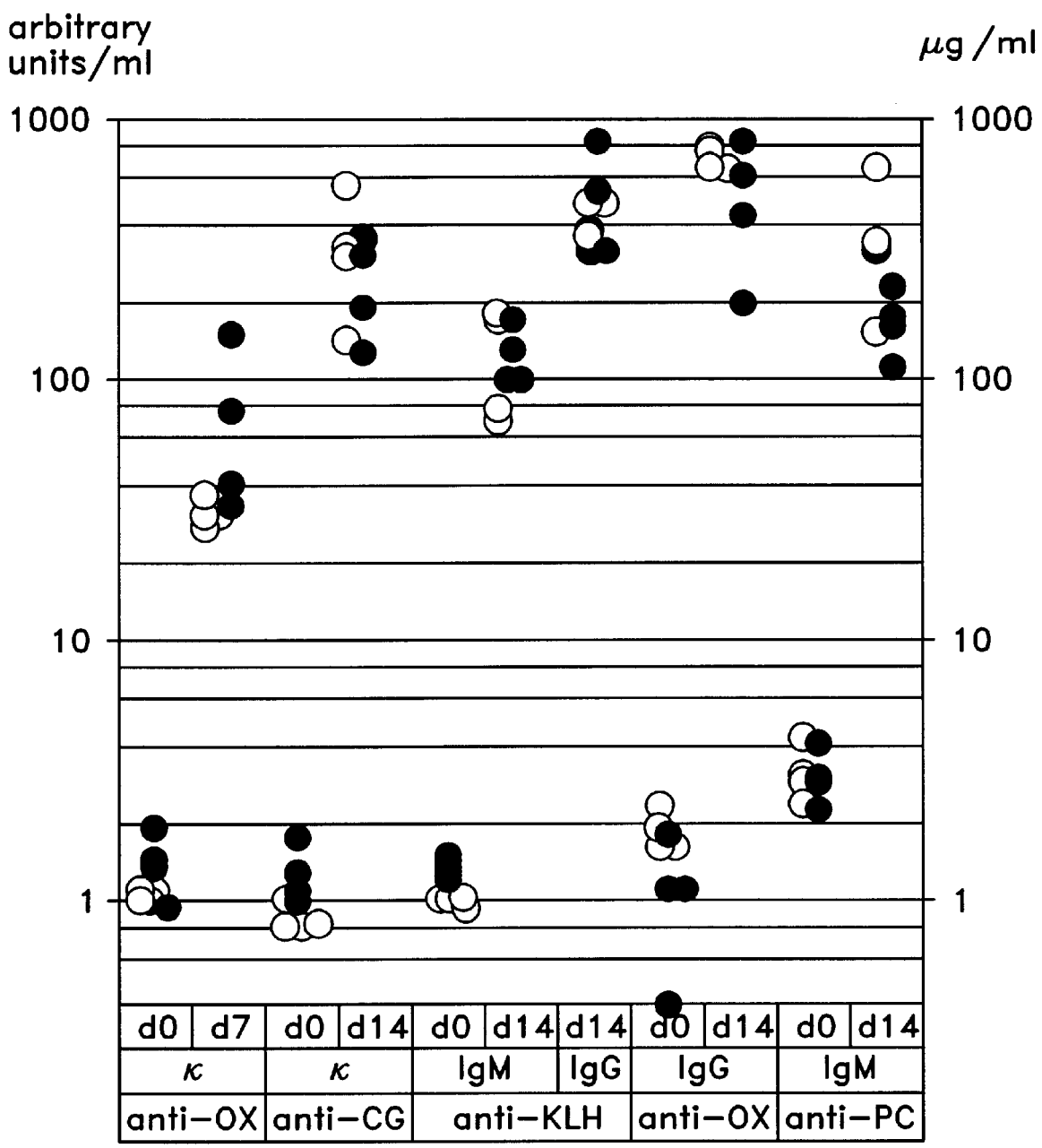
FIG. 4 is a graph showing the response of mice, having homozygous human $C\kappa$ gene replacement, to immunization with several defined antigens.

Serum antibodies were measured at the time of immunization and on days 7 and 14 after immunization. The data in FIG. 4 shows the antibody measurements from homozygous human Cκ mice (●) and control mice (○). It is clear from the results that the response of the mutants to any of these antigens is equivalent to that of wild-type mice, both in terms the levels of k chain bearing antibodies and the production of different isotypes tested.

Analysis of Affinity Maturation

A fundamental feature of the antibody response is affinity maturation through somatic hypermutation of the gene segments encoding the antigen binding site, and subsequent selection of those B cells which express antibodies of increased affinity. The mutation frequency was analyzed in rearranged VK genes expressed by B cells responding to immunization with phOX-CSA. Fourteen days after immunization, these cells are known to be contained in a B cell subset which can be brightly stained by phycoerythrin (PE)-labeled peanut agglutinin (PNA). They are also known to dominantly express a particular Vκ-Jκ rearrangement ($V\kappa_{OX1}$-$J\kappa_5$).

On day 14 of the phOX-CSA response, splenocytes from a CκR mutant mouse were isolated and stained with FITC-conjugated RA3-2B6 and PE-conjugated PNA, followed by sorting for the $PNA^{hi}$ B cell population. The purity of the sorted cells was 91%. cDNA sequences of $V\kappa_{OX1}$-$J\kappa_5$ were obtained and compared to the germline gene by the following method. Total cellular RNA was prepared from $1.8\times10^5$ $PNA^{hi}$ splenic B cells (as described in Gu et al. (1990) *EMBO J*. 9:2133). cDNA was synthesized using the Super Script Reverse Transcriptase kit (BRL). $V\kappa_{OX1}$-Jκ5 joints were then amplified with synthesis primers carrying the cloning sites of BAMHI and HindII. The primers were as follows: $V\kappa_{OX1}$ leader specific primer (SEQ ID NO:16) TGCGGATCCTCAGTCATAATATCCAG and $J\kappa_5$ primer (SEQ ID NO:17) CGGAATTCTTTCAGCTCCAGCTTGG. PCR was performed for 35 cycles. Each cycle consisted of 1 min. at 94°, 1 min. at 60°, and 1 min. at 74°. The amplified light chain fragments were cloned into the PTZ19R vector (Pharmacia, Uppsala).

The data is shown in Table 2. The data revealed that 66% of the sequences had mutations in the $V\kappa_{OX1}$-$J\kappa_5$ region of the chimeric k chain. Several sequences carried the key mutations in codons 34 and 37, known to increase the affinity of phOX-binding antibodies by approximately 10-fold. The frequency of mutations (2 mutations/sequence) in the chimeric light chains is similar to previously published observations.

Taken together, the human $C_\kappa$ replacement mouse produces B lymphocytes which synthesize antibodies containing humanized κ chains at levels comparable to those of mouse κ chains in wild-type littermates. When immunized with various T cell-dependent antigens, the mutant and wild-type mice produce equal levels of κ chain bearing specific antibodies. Furthermore, antigen specific B cells homozygous for the CκR mutation undergo affinity maturation through somatic hypermutation to the same extent as documented for the wild-type Cκ gene.

TABLE 2

| | | | | | | CDR I | | | CDR II | | | | | | CDR III | | |
|---|---|---|---|---|---|---|---|---|---|---|---|---|---|---|---|---|---|
| | 11 M | 14 S | 19 V | 20 T | 23 C | 26 S | 31 Y | 34 H | 36 Y | 37 Q | 46 R | 52 S | 75 I | 80 A | 93 S | 94 N | 95 P |
| (SEQ ID NO:5) VK-OX1 | ATG | TCT | GTC | ACC | TGC | AGC | TAC | CAC | TAC | CAG | AGA | TCC | ATC | GCT | AGT | AAC | CCA |
| A | --- | --- | --- | --- | --- | --- | --- | --- | --- | --- | --- | --- | --- | --- | --- | --- | --- |
| B | --- | --- | --- | --- | --- | --- | --- | --- | --- | --- | --- | --- | --- | --- | --- | --- | --- |
| (SEQ ID NO:6) | --- | --- | --- | --- | --- | --- | --- | --- | --- | --- | --- | --- | --- | --- | --- | --- | --G |
| (SEQ ID NO:7) | --- | --- | --- | --- | --- | --- | --- | --- | --- | --- | --- | --- | --- | --- | --- | --- | --G |
| (SEQ ID NO:8) | --- | --- | --- | --- | --- | --- | --- | --- | --- | --- | --- | --- | --- | --- | --- | --T | --G |
| (SEQ ID NO:9) | --- | --- | --- | --- | --- | --- | --- | --- | --- | --- | G-- | --- | --- | --- | --- | --- | --G |
| (SEQ ID NO:10) | --- | --- | --- | T-- | --- | --- | --- | --- | --- | --- | --- | --- | --- | --- | -A- | --- | --- |
| (SEQ ID NO:11) | --- | --- | -C- | --- | --- | --- | --- | --- | -T- | --- | --- | --- | --- | --- | --- | --- | --G |
| (SEQ ID NO:12) | G-- | --- | --- | --- | --- | --- | --- | A-- | -T- | A-- | --- | --- | --- | --- | --- | --- | --- |
| (SEQ ID NO:13) | G-- | --- | --- | --- | --- | --- | --- | A-- | -T- | A-- | --- | --- | --- | --- | --- | --- | --G |
| (SEQ ID NO:14) | --- | --- | --- | --- | --- | --- | --- | --G | -T- | --- | --- | --- | G-- | --- | --C | --- | --- |
| (SEQ ID NO:15) | --- | -T- | --- | --- | C-- | -A- | -T- | --- | -T- | --- | --- | -T- | --- | --C | --- | --- | --G |

Analysis of Immunoglobulin Production in Human Cγ Mice

Peripheral blood lymphocytes were isolated from four mice (heterozygous for the Cγ1R mutation) through Ficoll gradient and cultured with 40 μg/ml LPS plus IL4. Culture supernatants were collected after 6 days, and the concentrations of mouse (mIgG1) and humanized IgG1 (hIgG1) were determined by ELISA as described.

TABLE 3

| IgG1 antibodies generated through in vitro class switch | | | | |
|---|---|---|---|---|
| mIgG1 (μg/ml) | 33 | 25 | 26 | 16 |
| hIgG1 (μg/ml) | 20 | 20 | 21 | 17 |

When switching to IgG1 expression is induced in vitro from B cells of mice heterozygous for the Cγ1 replacement, the levels of wild-type and humanized IgG1 secreted into the culture medium was similar. As expected, the IgG1 in the mutants could only be detected by anti-human, not anti-mouse antibodies. That the constant region of the secreted γ1 chain in the mutants is indeed fully encoded by the human Cγ1 gene was confirmed by cloning the corresponding DNA from splenic B cells by polymerase chain reaction, and sequencing.

When the double mutant Cγ1 replacement mice were immunized with various T cell dependent antigens (in which IgG1 is often the predominant antibody isotype), they produced as much specific IgG1 antibody as did wild-type mice. There also appeared to be no major difference in antibody quality: affinity maturation proceeded similarly in mutant and wild-type animals in the anti-3-nitro-4-hydroxy-phenylacetyl (NP) response. The data is shown in FIG. 5.

Figure 5A:
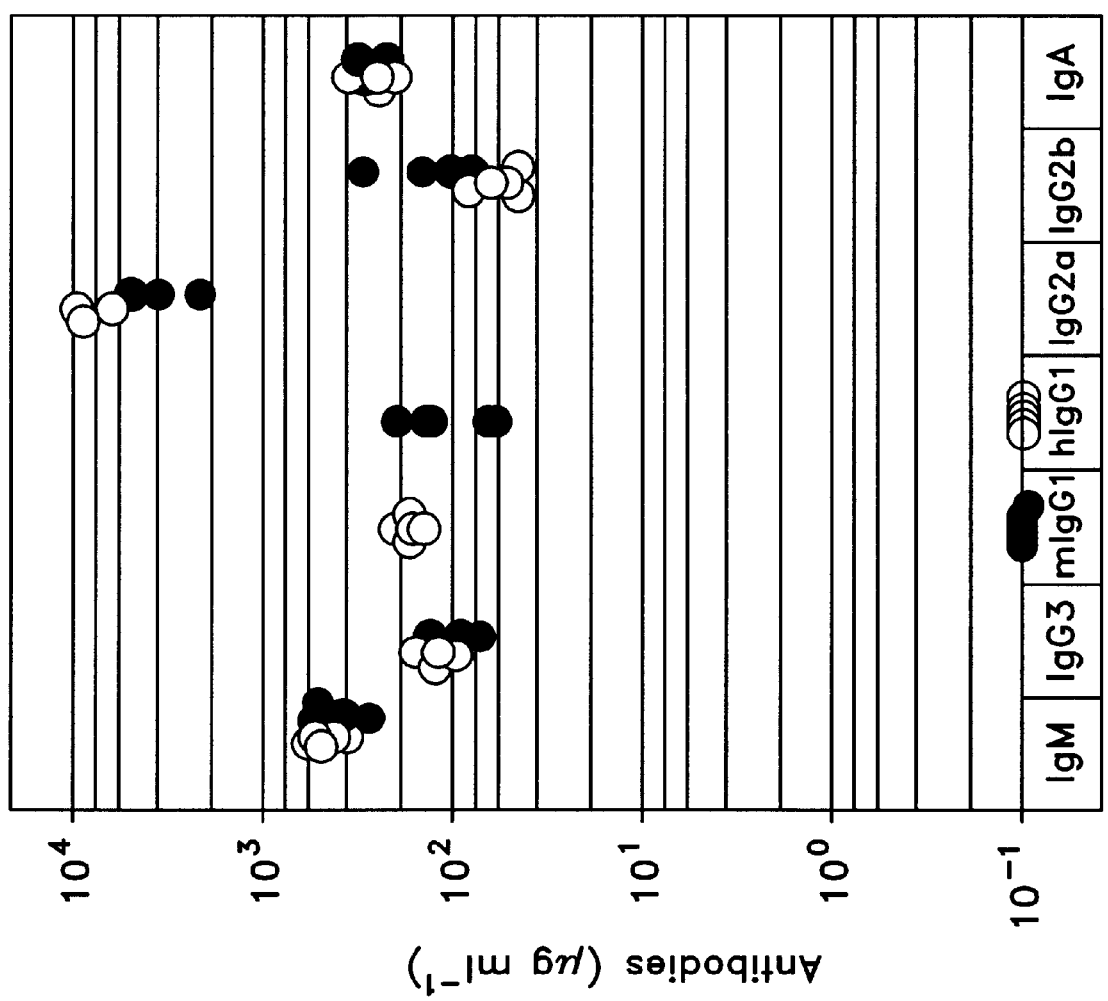
FIG. 5a shows serum concentrations of Ig isotypes in 7-week-old mutant mice.

Serum levels of antibodies of mutant and wild-type animals were determined by ELISA. Each symbol represents a value obtained from an individual mouse. FIG. 5A: Serum concentrations of Ig isotypes in 7-week-old mutant mice. Sera from 5-week-old wild-type 129 mice served as control. For the determination of humanized IgG1, plastic plates were coated with g)oat anti-human IgG antibodies (Jackson Immuno Research) and developed with mouse mAb anti-human IgG1 (clone 8c/6-39, The Binding Site, Birmingham, UK). ELISA was performed as described for all the other isotypes. The concentrations were calculated with mAbs of the respective isotypes as standards. The concentrations of light chain isotypes were determined as well, and the ratio of κ- to γ1-bearing antibodies in the mutant animals was found to be around 4.5, indicating that the majority of the heavy chains pair with the chimeric κ chains.

Figure 5B:
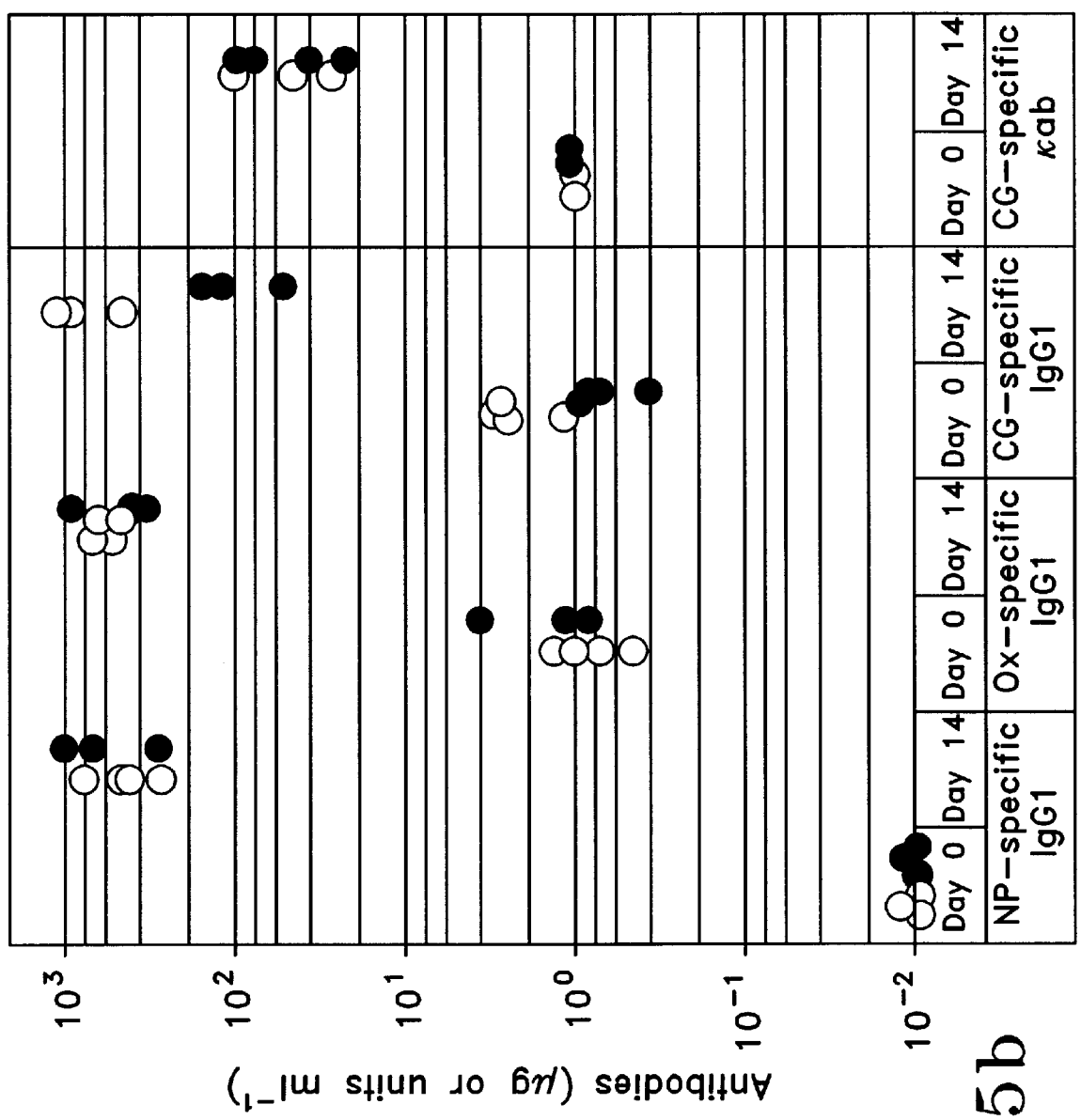
FIG. 5b shows serum levels of antigen binding antibodies.

FIG. 5B: Serum levels of antigen-binding antibodies. 9-week-old control and 6-week-old mutant animals received intraperitoneal injections of 100 μg of alum-precipitated NP-CG, phOX-CSA, mixed with $10^9$ Bordetella pertussis organisms. Sera were collected on day 14 after immunization. The left panel shows titers of antigen-specific IgG1 antibodies. The right panel depicts titers of CG-specific κ-bearing antibodies. In case of the anti-NP response, the concentration of NP-binding IgG1 was determined by comparison to monoclonal mouse as well as humanized IgG1 mAbs against NP (the latter raised by fusion of X63Ag8.653 myeloma cells with splenic B cells isolated from the NP-CG immunized mutant mice homozygous for both the CκR and Cγ1R mutations). The relative concentrations of OX-or CG-specific IgG1 and κ-bearing antibodies are shown as arbitrary units, taking the value of the serum from a preimmune normal or mutant animal as 1 unit.

Figure 5C:
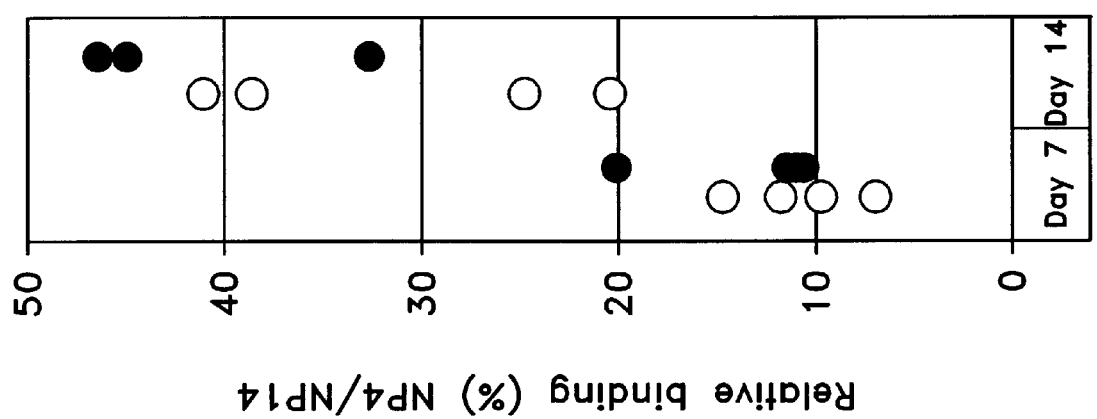
FIG. 5c shows relative affinities of antibodies.

FIG. 5C: Affinity maturation. Relative affinities of anti-NP IgG1 antibodies were measured using a plate binding assay which is based on the direct correlation of antibody affinity and the ratio of antibody-binding to NP-carrier conjugates at low ($NP_4BSA$) and high ($NP_{14}BSA$) hapten density. Relative affinities were determined at days 7 and 14 after immunization.

Analysis of Somatic Hypermutation in Human Cγ1 Replacment Mice

In order to confirm that the human Cγ1 replacement mutation does not interfere with the somatic hypermutation process, the sequence was determined. Germinal center B cells were isolated from oxalozone (Ox)-immunized mice on day 14 of the response by fluorescent cell sorting, using the B lineage surface marker B220/CD45R and the germinal center B cell specific marker peanut agglutinin. From these cells, mRNA encoding human γ1 constant regions and $V_H$ regions predominantly expressed in anti-Ox responses of IgH$^a$ allotype mice were amplified with the appropriate primers, cloned and sequenced. Somatic point mutations could be identified in most sequences at high frequency. In 6 $V_H$ gene sequences, there were 29 independent point mutations in 1740 base pairs sequenced, i.e. a mutation frequency of 1:60.

It is evident from the above results that the replacement of host immunoglobulin constant region genes with corresponding human genes generates a mouse strain that produces high levels of humanized antibodies. The animal host can be immunized to produce human antibodies or analogs specific for an immunogen. The B cells thus generated are able to undergo the process of class switching, and somatic mutation, to produce high affinity antibodies.

The subject invention provides for a convenient source of humanized antibodies. The problems associated with obtaining human monoclonal antibodies are avoided, since mice can be immunized with immunogens that could not be used with a human host. Humanized antibodies can be produced to human immunogens, e.g. proteins, by immunization of the subject mice with the human immunogens. The resulting antisera will be specific for the human immunogen and may be harvested from the serum of the host. One can also provide for booster injections and adjuvants which would not be permitted with a human host. The resulting B-cells may then be immortalized for the continuous production of the desired antibody.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of producing a transgenic mouse having a genome comprising a targeted, functional replacement of a mouse immunoglobulin constant region gene segment with a human immunoglobulin constant region gene segment comprising, selecting a transgenic mouse comprising a targeted, functional replacement of the mouse immunoglobulin constant region gene segment with said human immunoglobulin constant region gene segment, wherein said mouse is the progeny of a surrogate mother that contained a mouse blastocyst comprising a mouse embryonic stem cell, wherein said mouse embryonic stem cell was transfected with a recombination vector comprising a human immunoglobulin constant region gene segment, DNA sequences homologous to the mouse immunoglobulin constant region gene segment, a selectable marker gene and recombinase recognition sites flanking said selectable marker gene, wherein said selectable marker gene is removed by a non-mammalian recombinase.

2. The method of claim 1 wherein said embryonic stem cell expresses a non-mammalian recombinase.

3. The method of claim 1 wherein said immunoglobulin constant region gene segment is a heavy chain gene.

4. The method of claim 1 wherein said immunoglobulin constant region gene segment is a light chain gene.

5. The method of claim 1 wherein said recombinase recognition site is loxP and said recombinase is Cre recombinase.

6. The method of claim 1 wherein said recombinase recognition site is frt and said recombinase is Flip recombinase.

7. The method of claim 1 wherein said human constant region gene segment is from the Cγ1 gene.

8. The method of claim 1 wherein said human constant region gene segment is from the Ck gene.

9. A transgenic mouse made by the method of claim 1 and progeny of said mouse, wherein said mouse and said progeny have a genome comprising a targeted, functional replacement of a mouse immunoglobulin constant region gene segment with a human immunoglobulin constant region gene segment, wherein the genome of said mouse and said progeny lack said selectable marker gene of said method of claim 1, and wherein said mouse or said progeny produces antibodies comprising a human constant region joined to a mouse variable region in response to an antigen.

10. A method of producing a transgenic mouse having a genome comprising a targeted, functional replacement of a mouse immunoglobulin constant region gene segment with a human immunoglobulin constant region gene segment comprising the steps of:
  i) transferring a mouse blastocyst comprising a mouse embryonic stem cell into a surrogate mother, wherein said embryonic stem cell is transfected with a recombination vector comprising a human immunoglobulin constant region gene segment, DNA sequences homologous to the mouse immunoglobulin constant region gene segment, a selectable marker gene and recombinase recognition sites flanking said selectable marker gene, wherein said selectable marker gene is removed by a non-mammalian recombinase;
  ii) selecting surrogate mother progeny comprising a targeted, functional replacement of the mouse immunoglobulin constant region gene segment with said human immunoglobulin constant region gene segment.

11. The method of claim 10 wherein said embryonic stem cell expresses a non-mammalian recombinase.

12. A transgenic mouse made by the method of claim 10 and progeny of said mouse, wherein said mouse and said progeny have a genome comprising a targeted, functional replacement of a mouse immunoglobulin constant region gene segment with a human immunoglobulin constant region gene segment, wherein the genome of said mouse and said progeny lack said selectable marker gene of said method of claim 10, and wherein said mouse or said progeny produces antibodies comprising a human constant region joined to a mouse variable region in response to an antigen.

13. A transgenic mouse, or progeny thereof, having a genome comprising a targeted, functional replacement of a mouse immunoglobulin constant region gene segment with a human immunoglobulin constant region gene segment, wherein said transgenic mouse produces antibodies comprising a human constant region joined to a mouse variable region in response to an antigen.

14. A transgenic mouse, and progeny of said mouse, wherein said mouse is made by mating a transgenic mouse according to claim 13 with another transgenic mouse according to claim 13, wherein said mouse has a genome comprising a targeted, functional replacement of a mouse immunoglobulin constant region gene segment with a human immunoglobulin constant region gene segment, and wherein said mouse or said progeny produce antibodies comprising a human constant region joined to a mouse variable region in response to an antigen.

15. The transgenic mouse of claim 13 wherein said immunoglobulin constant region gene segment is a light chain gene.

16. The transgenic mouse of claim 13 wherein said immunoglobulin constant region gene segment is a heavy chain gene.

17. The transgenic mouse according to claim 13 wherein said human immunoglobulin constant region gene segment is present on both chromosomes.

18. The transgenic mouse according to claim 13, wherein said antibodies comprising a human constant region joined to a mouse variable region are produced at levels of at least 50 μg/ml in said mouse serum.

19. The transgenic mouse according to claim 13, wherein said human immunoglobulin constant region gene segment is from the Cγ1 gene.

20. The transgenic mouse according to claim 13, wherein said human immunoglobulin constant region gene segment is from the Ck gene and wherein said antibodies are produced at levels of at least 500 μg/ml in said mouse serum.

21. The transgenic mouse according to claim 13, wherein said mouse comprises a human Cκ gene segment inserted at the locus for an endogenous mouse immunoglobulin light chain constant region gene segment on both chromosomes and a human Cγ1 constant region gene segment, wherein said antibodies produced comprise domains from human Ck, and human Cγ1.

22. A method for producing humanized antibodies in response to an antigen, comprising the step of selecting antibodies comprising a human constant region gene segment from a transgenic mouse immunized with said antigen, said mouse having a genome comprising a targeted, functional replacement of a mouse immunoglobulin constant region gene segment with a human immunoglobulin constant region gene segment, wherein said transgenic mouse produces antibodies comprising a human constant region joined to a mouse variable region in response to an antigen.

23. The method of claim 22 wherein said immunoglobulin constant region gene segment is a light chain gene.

24. The method of claim 22 wherein said immunoglobulin constant region gene segment is a heavy chain gene.

25. The method of claim 22 wherein said human immunoglobulin constant region gene segment is present on both chromosomes.

26. The method of claim 22, wherein said antibodies comprising a human constant region joined to a mouse variable region are produced at levels of at least 50 μg/ml in said mouse serum.

27. The method of claim 22, wherein said human immunoglobulin constant region gene segment is from the Cγ1 gene.

28. The method of claim 22, wherein said human immunoglobulin constant region gene segment is from the Cκ gene and wherein said antibodies are produced at levels of at least 500 μg/ml.

29. The method of claim 22, wherein said mouse comprises a human Ck gene segment inserted at the locus for an endogenous mouse immunoglobulin light chain constant region gene segment on both chromosomes and a human Cγ1 constant region gene segment, wherein said antibodies produced comprise domains from human Ck, and human Cγ1.

30. A method for producing humanized antibodies in response to an antigen, comprising the steps of:
  i) immunizing a transgenic mouse with said antigen, said mouse containing a genome comprising a targeted, functional replacement of a mouse immunoglobulin constant region gene segment with a human immunoglobulin constant region gene segment, wherein said transgenic mouse produces antibodies comprising a human constant region joined to a mouse variable region in response to said antigen; and
  ii) selecting antibodies comprising a human constant region gene segment.

31. A method of producing a transgenic mouse comprising a human immunoglobulin light chain gene segment and a human immunoglobulin heavy chain gene segment comprising mating a first transgenic mouse having a genome comprising a targeted, functional replacement of a mouse immunoglobulin constant region gene segment with a human immunoglobulin constant region gene segment, wherein in said first transgenic mouse, said human immunoglobulin constant region gene segment is from the Cγ1 gene, with a second transgenic mouse having a genome comprising a targeted, functional replacement of a mouse immunoglobulin constant region gene segment with a human immunoglobulin constant region gene segment, wherein in said second transgenic mouse said human immunoglobulin constant region gene segment is from the Ck gene and selecting progeny that comprises a gene segment from the Cγ1 gene and a gene segment from the Ck gene.

* * * * *

```
                          SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION:  SEQ ID NO: 1:

CAGGATCCAA CTGTATCCAT C                                             21

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION:  SEQ ID NO:  2:

GAGGTACCAA GGAAAGGGAG G                                             21

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION:  SEQ ID NO:  3:
```

TTATCGATAC AGAGGCTCAA CCTACAAA                                        28

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

CCAAGCTTCG CTACTTTTGC ACCCTT                                          26

(2) INFORMATION FOR SEQ ID NO:5:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

ATGTCTGTCA CCTGCAGCTA CCACTACCAG AGATCCATCG CTAGTAACCC A              51

(2) INFORMATION FOR SEQ ID NO:6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

ATGTCTGTCA CCTGCAGCTA CCACTACCAG AGATCCATCG CTAGTAACCC G              51

(2) INFORMATION FOR SEQ ID NO:7:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

ATGTCTGTCA CCTGCAGCTA CCACTACCAG AGATCCATCG CTAGTAACCC G              51

(2) INFORMATION FOR SEQ ID NO:8:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

ATGTCTGTCA CCTGCAGCTA CCACTACCAG AGATCCATCG CTAGTAATCC G              51

(2) INFORMATION FOR SEQ ID NO:9:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 9:

ATGTCTGTCA CCTGCAGCTA CCACTACCAG GGATCCATCG CTAGTAACCC G     51

(2) INFORMATION FOR SEQ ID NO:10:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

ATGTCTGTCT CCTGCAGCTA CCACTACCAG AGATCCATCG CTAATAACCC A     51

(2) INFORMATION FOR SEQ ID NO:11:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

ATGTCTGCCA CCTGCAGCTA CCACTATCAG AGATCCATCG CTAGTAACCC G     51

(2) INFORMATION FOR SEQ ID NO:12:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

GTGTCTGTCA CCTGCAGCTA CAACTTCAAG AGATCCATCG CTAGTAACCC A     51

(2) INFORMATION FOR SEQ ID NO:13:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GTGTCTGTCA CCTGCAGCTA CAACTTCAAG AGATCCATCG CTAGTAACCC G     51

(2) INFORMATION FOR SEQ ID NO:14:

(i) SEQUENCE CHARACTERISTICS:
        (A) LENGTH: 51 base pairs
        (B) TYPE: nucleic acid -continued

```
            (C) STRANDEDNESS: single
            (D) TOPOLOGY: linear (ii) MOLECULE TYPE: cDNA (xi) SEQUENCE DESCRIPTION: SEQ ID NO: 14:

ATGTCTGTCA CCTGCAGCTA CCACTAGCTG AGATCCATGG CTAGCAACCC A         51

(2) INFORMATION FOR SEQ ID NO:15:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 15:

ATGTTTGTCA CCCGCAACTT CCACTTCCAG AGATTCATCG CCAGTAACCC G         51

(2) INFORMATION FOR SEQ ID NO:16:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 16:

TGCGGATCCT CAGTCATAAT ATCCAG                                     26

(2) INFORMATION FOR SEQ ID NO:17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 17:

CGGAATTCTT TCAGCTCCAG CTTGG                                      25
```